United States Patent
Kirenko et al.

(10) Patent No.: US 10,398,328 B2
(45) Date of Patent: Sep. 3, 2019

(54) DEVICE AND SYSTEM FOR MONITORING OF PULSE-RELATED INFORMATION OF A SUBJECT

(71) Applicant: KONINKLIJKE PHILIPS N.V., Eindhoven (NL)

(72) Inventors: Ihor Olehovych Kirenko, Veldhoven (NL); Ronaldus Maria Aarts, Geldrop (NL); Caifeng Shan, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 295 days.

(21) Appl. No.: 15/241,846

(22) Filed: Aug. 19, 2016

(65) Prior Publication Data
US 2017/0055853 A1    Mar. 2, 2017

(30) Foreign Application Priority Data

Aug. 25, 2015 (EP) .................................... 15182289

(51) Int. Cl.
*A61B 5/02* (2006.01)
*A61B 5/024* (2006.01)
(Continued)

(52) U.S. Cl.
CPC ........ *A61B 5/02427* (2013.01); *A61B 5/0002* (2013.01); *A61B 5/0017* (2013.01);
(Continued)

(58) Field of Classification Search
CPC .. A61B 5/0205; A61B 5/0816; A61B 5/02416
See application file for complete search history.

(56) References Cited

U.S. PATENT DOCUMENTS

2011/0077486 A1*  3/2011  Watson ................. A61B 5/021
                                                            600/324
2014/0276104 A1   9/2014  Tao et al.
(Continued)

FOREIGN PATENT DOCUMENTS

KR    20150016903 A    2/2015
WO    2015018675 A1    2/2015
(Continued)

OTHER PUBLICATIONS

Wong, et al., "Contactless Recording oh Photoplethysmogram on a Sleeping Bed", Proceedings of the 31st Annual International Conference of the IEEE EMBS, Sep. 3, 2009, pp. 907-910.

*Primary Examiner* — Michael J D Abreu

(57) ABSTRACT

Various embodiments relate to a wearable device for obtaining signals from a subject for use in the monitoring of pulse-related information of the subject. To enable the use of such a device in the monitoring of pulse-related information, which provides for unobtrusive, reproducible, easy to use, and simple measurements, the device comprises a body, a PPG signal sensing unit for acquiring a first PPG signal from a first body location of the subject, and an imaging unit for acquiring a sequence of images from a second body location of the subject's body different from the first body location, said sequence of images being configured for deriving a second PPG signal for the second body location of the subject. Said PPG signal sensing unit and said imaging unit are mounted in or at the device body and are configured to simultaneously acquire the first PPG signal and the sequence of images.

13 Claims, 6 Drawing Sheets

(51) Int. Cl.
*A61B 5/021* (2006.01)
*A61B 5/00* (2006.01)
*A61B 5/026* (2006.01)
*A61B 5/0295* (2006.01)
*A61B 5/1455* (2006.01)

(52) U.S. Cl.
CPC .......... *A61B 5/0024* (2013.01); *A61B 5/0077* (2013.01); *A61B 5/0261* (2013.01); *A61B 5/0295* (2013.01); *A61B 5/02125* (2013.01); *A61B 5/02433* (2013.01); *A61B 5/02438* (2013.01); *A61B 5/14552* (2013.01); *A61B 5/681* (2013.01); *A61B 5/6803* (2013.01); *A61B 5/6824* (2013.01); *A61B 5/6843* (2013.01); *A61B 5/6844* (2013.01); *A61B 5/6898* (2013.01); *A61B 5/7278* (2013.01)

(56) References Cited

U.S. PATENT DOCUMENTS

| | | | |
|---|---|---|---|
| 2015/0051521 A1 | 2/2015 | Woerlee et al. | |
| 2015/0148636 A1 | 5/2015 | Benaron | |
| 2015/0182132 A1* | 7/2015 | Harris | A61B 5/0295 340/870.01 |
| 2017/0011210 A1* | 1/2017 | Cheong | H04W 12/06 |

FOREIGN PATENT DOCUMENTS

| | | | |
|---|---|---|---|
| WO | 2015078735 A1 | 6/2015 | |
| WO | 2015086338 A1 | 6/2015 | |

* cited by examiner

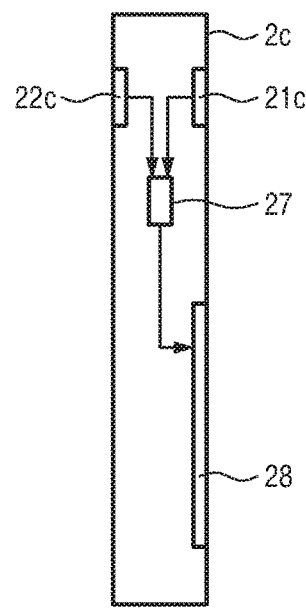
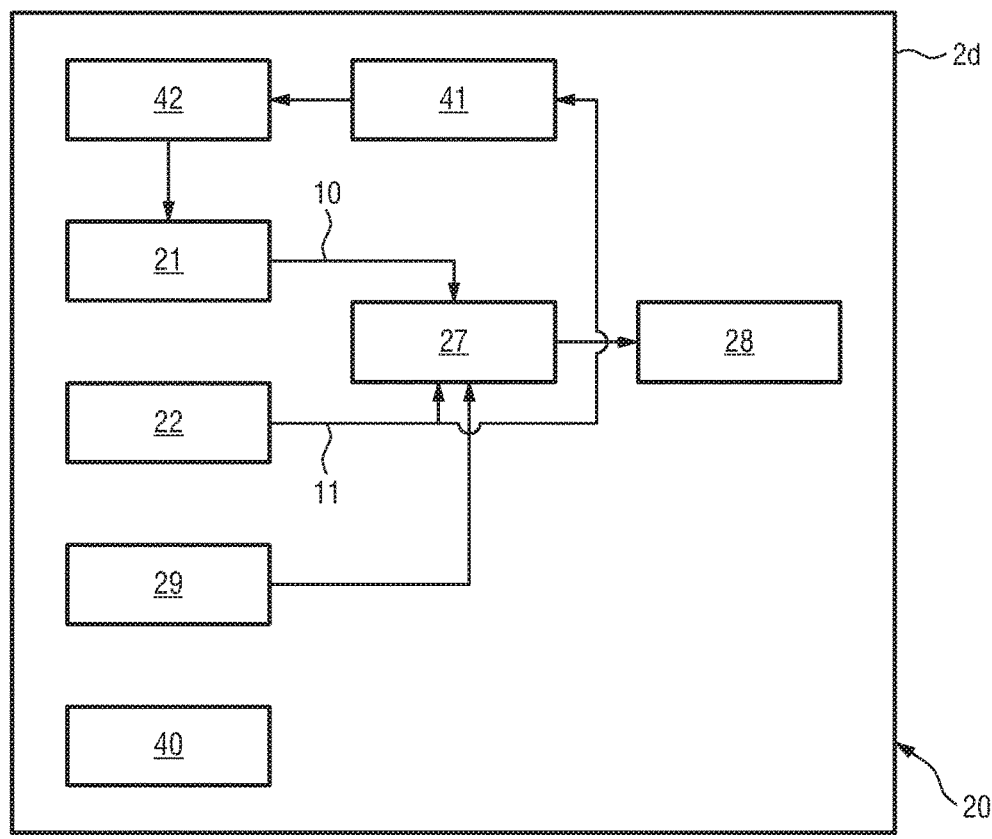
FIG.6
FIG.7

DEVICE AND SYSTEM FOR MONITORING OF PULSE-RELATED INFORMATION OF A SUBJECT

FIELD OF THE INVENTION

The present invention relates to a wearable device for obtaining signals from a subject for use in the monitoring of pulse-related information of the subject. Further, the present invention relates to a system for monitoring of pulse-related information of a subject.

BACKGROUND OF THE INVENTION

Vital signs of a person, for example the heart rate (HR), the respiration rate (RR) or the arterial blood oxygen saturation (SpO2), serve as indicators of the current health state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heartbeat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmittance and/or reflectivity at different wavelengths (typically red and infrared), the blood oxygen saturation (SpO2) can be determined. Different kinds of such contact sensor are commonly known and used, including contact finger pulse oximeters, contact forehead pulse oximeter sensors, contact pulse sensors, etc.

Recently, non-contact, remote photoplethysmography (rPPG) devices (also called camera PPG devices) for unobtrusive measurements have been described in many publications, e.g. in Verkruysse et al., "Remote plethysmographic imaging using ambient light", Optics Express, 16(26), 22 Dec. 2008, pp. 21434-21445, which demonstrates that photoplethysmographic signals can be measured remotely using ambient light and a conventional consumer level video camera, using red, green and blue color channels.

Remote PPG utilizes light sources or, in general radiation sources, disposed remotely from the subject of interest. Similarly, also a detector, e.g., a camera or a photo detector, can be disposed remotely from the subject of interest, i.e. without contact to the subject. Therefore, remote photoplethysmographic systems and devices are considered unobtrusive and well suited for medical as well as non-medical everyday applications. This technology particularly has distinct advantages for patients with extreme skin sensitivity requiring vital signs monitoring such as Neonatal Intensive Care Unit (NICU) patients with extremely fragile skin or premature babies.

Current methods for evaluation of blood pressure changes are based on measurement of pulse transit time (PTT) or pulse arrival time (PAT). The first approach estimates the transit time between one signal carrying the arterial pulse wave (pulse wave signal) and another signal such as the electrocardiogram (ECG). The time interval between the ECG fiducial point (typically the R peak) and a fiducial point marking the pulse arrival is referred to as the PAT. The PTT is the time difference between the aortic valve opening and the pulse wave arrival. The second approach estimates the BP from the PTT between two pulse wave signals measured at different parts of the body.

These methods require placement of contact PPG (and/or ECG) sensors at two body locations, at least, preferably at large distance from each other. This might require significant time investment and efforts to estimate changes of blood pressure based on PTT. Moreover, in order to follow the trend of changes of blood pressure over long periods of time (e.g. days), the location for placement of contact sensors, as well as position of a body should be the same for every measurement. Furthermore, the two sensors needs to be synchronized to millisecond level in order to provide accurate PTT measurement. Finally, contact sensors are sensitive to motion of a person, and are sensitive to correct placement.

Those disadvantages of current methods of PTT measurement limit the use of such approach beyond professional healthcare environment (e.g. at home, on the go, etc.). Therefore, there is a need for a system, which can remove disadvantages of current systems for PTT-based measurement of pulse-related information such as e.g. blood pressure changes, pulse transit time and/or pulse arrival time.

SUMMARY OF THE INVENTION

It is an object of the present invention to provide a wearable device for obtaining signals from a subject for use in the monitoring of pulse-related information of the subject, which provides for unobtrusive, reproducible, easy to use, and simple measurements, preferably using existing type of devices that are used in everyday life. Further, it is another object of the present invention to provide a corresponding system for monitoring of pulse-related information of a subject.

In a first aspect of the present invention a wearable device for obtaining signals from a subject for use in the monitoring of pulse transit time and/or pulse arrival time is presented. The wearable device includes a device body, a PPG signal sensing unit for acquiring a first photoplethysmography, PPG, signal from a first body location of the subject's body, wherein the first PPG signal sensing unit is in contact with the first location, and an imaging unit for acquiring a sequence of images from a second body location of the subject's body different from the first body location, said sequence of images being configured for deriving a second PPG signal for the second body location of the subject's body, wherein said PPG signal sensing unit and said imaging unit are mounted in or at the device body and are configured to simultaneously acquire the first PPG signal and the sequence of images, a processing unit for deriving the second PPG signal from said sequence of images, wherein the processing unit is configured to determine the pulse transit time and/or pulse arrival time based on the first PPG signal and the second PPG signal.

In a further aspect of the present invention a system for monitoring of pulse transit time and/or pulse arrival time is presented, the system comprising a wearable device comprising a PPG signal sensing unit for acquiring a first photoplethysmography, (PPG), signal from a first body location of the subject's body, wherein the first PPG signal sensing unit is in contact with the first location;

an imaging unit for acquiring a sequence of images from a second body location of the subject's body different from the first body location, said sequence of images being configured for deriving a second PPG signal for the second body location of the subject's body; and an output unit for outputting said first PPG signal and said sequence of images, wherein the said outputted first PPG signal and sequence of images are sent to another entity for processing via a communication network, wherein the another entity comprising: an input unit for obtaining the first PPG signal and the sequence of images acquired by the wearable device via the communications network, and a processor for deriving a second PPG signal from said sequence of images and for determining the pulse transit time and/or pulse arrival time from said first and second PPG signals.

Preferred embodiments of the invention are defined in the dependent claims. It shall be understood that the claimed system has similar and/or identical preferred embodiments as the claimed device and as defined in the dependent claims.

The present invention is based on the idea to make use of the benefits of remote and reflective PPG approaches to design a new PPG sensor arrangement combining two separate sensors enabling simultaneously obtaining two PPG signals from different portions of the user's body in a simple, unobtrusive, reproducible, easy to use manner. The proposed wearable device thus comprises two separate sensor units, wherein at least one of the sensor units is an imaging unit, such as a 2D camera or 2D image sensor. The two sensor units are e.g. placed at different sides of a device to obtain separate sensor signals (PPG signals) from different body locations. In this way pulse-related information of the subject can be obtained particularly including one or more of pulse transit time, pulse arrival time, pulse wave velocity, hemodynamic information and/or blood pressure changes of the subject.

Contrary to known systems using several contact PPG sensors placed on body parts (e.g. legs, arms, forehead), synchronized with each other or/and with ECG, all the information used according to the present invention comes from one single wearable device.

The present invention provides a reliable and efficient device and system that can provide pulse-related information automatically, continuously and in a non-obtrusive way. It enables a continuous measurement of transit time of a pressure pulse when travelling through the body. Further, pulse transit time (PTT) can be determined and pulse wave velocity (PWV) values can be calculated, e.g. in the following way:

PWV=D/PTT, where D is the distance difference between the travelling distances from the heart to the points of measurement (i.e. the points of measurement of the first PPG signal and the sequence of images, in particular the particular region within the images, from which the second PPG signal is derived). For instance, if the PAT of face and hand are measured, the distance D corresponds to the distance difference between "travelling distance from heart to face" and "travelling distance from heart to hand". The pulse transit time is generally defined as:

PTT=PATd−PATp, where PATp is the pulse arrival time (PAT) of the pressure pulse at the point closer to the heart and PATd is the arrival time of the pressure pulse at extremity. Using signals from various body sites, e.g. from the forehead and hand, allows to detect PTT measurements, which are not affected by the pre-ejection period (PEP). More precisely, in mathematical terms, taking the difference of at least two measured PAT cancels the PEP contribution and only the PTT difference remains. Alternatively, calculation of the PTT can be done in the frequency domain.

Further, according to the present invention PAT measures can be obtained and hemodynamic information about the hemodynamic status of the subject can be derived from said one or more PAT measures. Non-limiting examples of such PAT measures are the PAT foot, PAT 20%, PAT50%, PAT80%, the PAT top, the PTT and/or the PEP. From a combination of the acquired signals such PAT measures can be easily obtained and monitored to detect changes of the hemodynamic status of the subject.

Further, changes of blood pressure can be monitored based on analysis of changes of PTT and PAT values. The calculation itself is generally known, e.g. from WO 2013/171599 A1, WO 2010/020914 A1 or WO 2009/136341 A2. Generally, the pulse arrival time (PAT) is the sum of the pre-ejection period (PEP), determined by a measure of the aortic closure and pulse transit time (PTT), as e.g. described in X. Aubert, J. Muehlsteff, "Non-Invasive Cuff-less Measurements of the Arterial Blood Pressure: What does Pulse-Transit-Time tell us all about?", Proc. ESGCO '06, Jena, Germany, May 2006 and J. Muehlsteff, X. Aubert, M. Schuett, "Cuff-less Estimation of Systolic Blood Pressure for Short Effort Bicycle Tests: The Prominent Role of the Pre-Ejection Period", EMBC '06, New York, 2006.

A definition how to obtain the blood pressure can e.g. be found in B M McCarthy, B O'Flynn and A Mathewson "An Investigation of Pulse Transit Time as a Non-Invasive Blood Pressure Measurement Method", J. Phys.: Conf. Ser. 307 012060 as follows: Blood pressure can be related to PTT directly by $$P_e = P_b - \frac{2}{\gamma PTT_b} \Delta PTT$$

where $P_b$ is the base blood pressure level, $PTT_b$ is the value of PTT corresponding to the pressure $P_b$, while $\Delta PTT$ is the change in the PTT and y is a coefficient ranging from 0.016 to 0.018 (mmHg$^{-1}$).

The proposed device may e.g. be wrist worn device, such as a watch, at which the two sensor units are placed in a way to provide a view on two different body parts, such as for instance face and wrist of a person. Therefore, a practical embodiment of such device may be a watch placed on a wrist of a subject with a 2D optical sensor on top of the watch and another optical sensor on the bottom. In this embodiment, estimation of PTT is achieved by measuring PPG signals from a face of a person and from the wrist, followed by an analysis of the time delay between peaks of the detected pulse signals to extract PTT (or PAT).

Another practical embodiment of such device may be a head-mounted device (such as Google Glass) worn by a subject on his/her head. The device may have two optical sensors, one looking forward (outward), and another one looking backward (inward). The forward-looking sensor may preferably be a 2D camera sensor to remotely measure PPG signals at a body part such as a hand. The backward-looking sensor is looking at a skin area in face or is attached to a skin area in face, i.e. can be either a 2D camera sensor or a single spot photo-sensor. In this way, PTT may be estimated by measuring PPG signals at two different body parts. Similar to above embodiment, an analysis of the time delay between peaks of the detected pulse signals provides PTT and/or PAT.

Further pulse-related signals can be derived from the PPG signals and the extracted PTT in both embodiments.

In an embodiment the device further comprises an output unit for outputting said first PPG signal and said sequence of images for processing by another entity. The other entity may e.g. be a computer, tablet, smartphone, central server (e.g. of a hospital), or generally any device of e.g. the user, a caregiver or a physician.

In another embodiment the device further comprises a processing unit for deriving a second PPG signal from said sequence of images and for determining pulse-related information from said first and second PPG signals.

There are various options for implementing the PPG signal sensing unit. In one embodiment said PPG signal sensing unit comprises an optical sensing unit, in particular a contact sensor. In another embodiment said PPG signal sensing unit comprises another imaging unit. It depends on the particular application, costs, use etc. how the PPG signal sensing unit may preferably be implemented.

The distance difference between the travelling distances from the heart to said first and second body locations, respectively, may generally be known or estimated, e.g. based on the information at which position of the device body the PPG signal sensing unit and the imaging unit are arranged and which direction they are oriented, which allows an estimation from which body location the respective signal will be obtained. In another embodiment the device may further comprise a distance unit for obtaining the distance between said first and second body locations and/or the distances between the first body location and the second body location, respectively, and the heart, wherein said processing unit is configured to use the obtained distance(s) in determining the pulse-related information. For instance, from said distances the distance difference between the travelling distances from the heart to said first and second body locations can be determined, which is then used in determining the pulse-related information. Alternatively, the distance unit may be configured to directly obtain the different distances between the respective body location and the heart, from which the distance difference can then be obtained. The use of such a distance unit increases the accuracy of the determination of the distance, which leads to more accurate results of the determined pulse-related information.

Said distance unit may thus be configured to obtain the distance through measurement, in particular from an image or the sequence of images acquired by the imaging unit, or through input from e.g. the user. Hence, image processing may be used to recognize the body portions and, there from, to determine the distance between them and/or the distance of the respective body portion to the heart, or the distances and/or the distance difference may directly be estimated within one or more images of the sequence of images.

In a preferred embodiment the device further comprises an illumination unit mounted in or at the device body for illuminating said first and/or second body location. The illumination unit may be a source of multi-wavelength dedicated illumination. It may e.g. be attached to a skin area or placed close to a skin area; it may e.g. be arranged next to the PPG signal sensing unit and/or the imaging unit to illuminate the respective body portion from which the respective signal is acquired.

The device may further comprise an image recognition unit for detecting when said second body part is shown in the images of the acquired sequence of images and a control unit for controlling the PPG signal sensing unit to start acquiring the first PPG signal if it is detected that the second body part is shown in an image. Hence, according to this embodiment, the device can start measurement when the skin area of the other body part (such as face, hand, wrist, elbow, leg) appears in the field of view of the imaging unit and can stop measurements when no skin area appears any more in the field of view. This particularly saves battery power and processing power.

The device may further comprise mounting equipment for mounting the device body at the subject's body. This may e.g. include a strap, wristband, headband, body band, etc., i.e. any kind of equipment, by which the device can be held at the subject's body.

As already mentioned briefly, said wearable device may be a wrist worn device, in particular a watch or heart rate monitor, glasses, camera, multimedia player, mobile phone or smart phone. Generally, any device, which allows mounting of the two sensing units such that they can simultaneously acquire separate PPG signals from different body locations, can be used.

In yet another embodiment there may be made use of a wrist worn device having a built in PPG sensor, which communicates with the other sensors in any of the above mentioned embodiment. Hereby, using the time difference between both sensors will lead to the PTT.

In a practical implementation said wearable device is a wrist worn device, wherein said PPG signal sensing unit is arranged at the bottom of the device body and the imaging unit is arranged at the front or a side surface of the device body.

In a practical implementation said PPG signal sensing unit is mounted at a first position in or at the device body facing said first body location when the wearable device is worn by the subject and said imaging unit is mounted at a second position in or at the device body facing said second body location when the wearable device is worn by the subject.

BRIEF DESCRIPTION OF THE DRAWINGS

These and other aspects of the invention will be apparent from and elucidated with reference to the embodiment(s) described hereinafter. In the following drawings FIG. 1 schematically shows a first embodiment of a system and device according to the present invention.

FIG. 6 shows a fourth embodiment of a device according to the present invention in the form of a smartphone, and FIG. 7 schematically shows a fifth embodiment of a device according to the present invention.

DETAILED DESCRIPTION OF THE INVENTION

Figure 1:
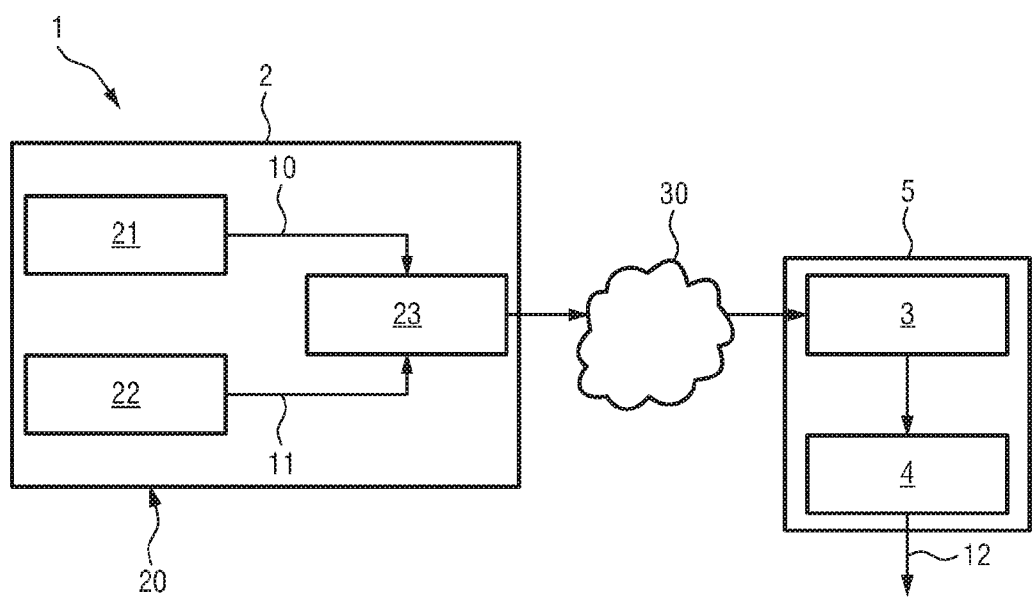

FIG. 1 schematically shows a first embodiment of a system 1 and a device 2 according to the present invention. The system 1 for monitoring of pulse transit time, pulse arrival time and/or blood pressure of a subject comprises a wearable device 2 for obtaining signals from a subject for use in the monitoring of pulse-related information, such as pulse transit time, pulse arrival time, blood pressure, pulse wave velocity and/or hemodynamic status of the subject. Detailed practical embodiments of such a wearable device will be explained in more detail below. The system 1 further comprises an input unit 3, e.g. a (wireless or wired) data interface, for obtaining (i.e. receiving or retrieving) a first PPG signal 10 and a sequence of images 11 acquired by the wearable device 2 and a processor 4 for deriving a second PPG signal from said sequence of images 11 and for determining, as output signal 12, the desired pulse-related information from said first and second PPG signals.

In one embodiment the elements of the system 1 are integrated into a common device together with the wearable device 2, e.g. the input unit 3 and the processor 4 may be integrated into the wearable device 2. In another embodiment, as shown in FIG. 1, the input unit 3 and the processor 4 may be arranged separate from the wearable device 2, e.g. in a computer 5 or workstation, to which the data acquired by the wearable device 2 are transmitted (e.g. via a network, such as Bluetooth, Wifi or a communications network).

The wearable device 2 comprises a device body 20, a PPG signal sensing unit 21 for acquiring the first PPG signal 10 from a first body location of the subject's body and an imaging unit 22, e.g. a camera, for acquiring the sequence of images 11 from a second body location of the subject's body different from the first body location. Hereby, said sequence of images is configured for deriving the second PPG signal for the second body location of the subject's body. The PPG signal sensing unit 21 and the imaging unit 22 are mounted in or at the device body 20 and are configured to simultaneously acquire the first PPG signal 10 and the sequence of images 11.

In the embodiment shown in FIG. 1 the wearable device 2 comprises an output unit 23 for outputting said first PPG signal 10 and said sequence of images 11 for processing by another entity, such as the computer 5, a wireless communication device/a mobile communication device, a remote server(s), etc. The computer 5 may be arranged at a separate location, e.g. at a caregiver, doctor or hospital, to which the data are transmitted, e.g. via a communications network or the internet 30. The processor may also be located in the cloud and may return the result of the calculation back to the wearable device 2 for presenting the result to the user or another person.

Generally, said PPG signal sensing unit 21 may be any kind of sensing unit that is able to acquire a PPG signal from the subject's body. The PPG sensing unit comprises an optical sensing unit, in particular a contact sensor (e.g. a pulse oximeter as conventionally used in a finger clip sensor or in a wristband). In another embodiment the PPG sensing unit comprises another imaging unit, e.g. another camera.

Figure 2:
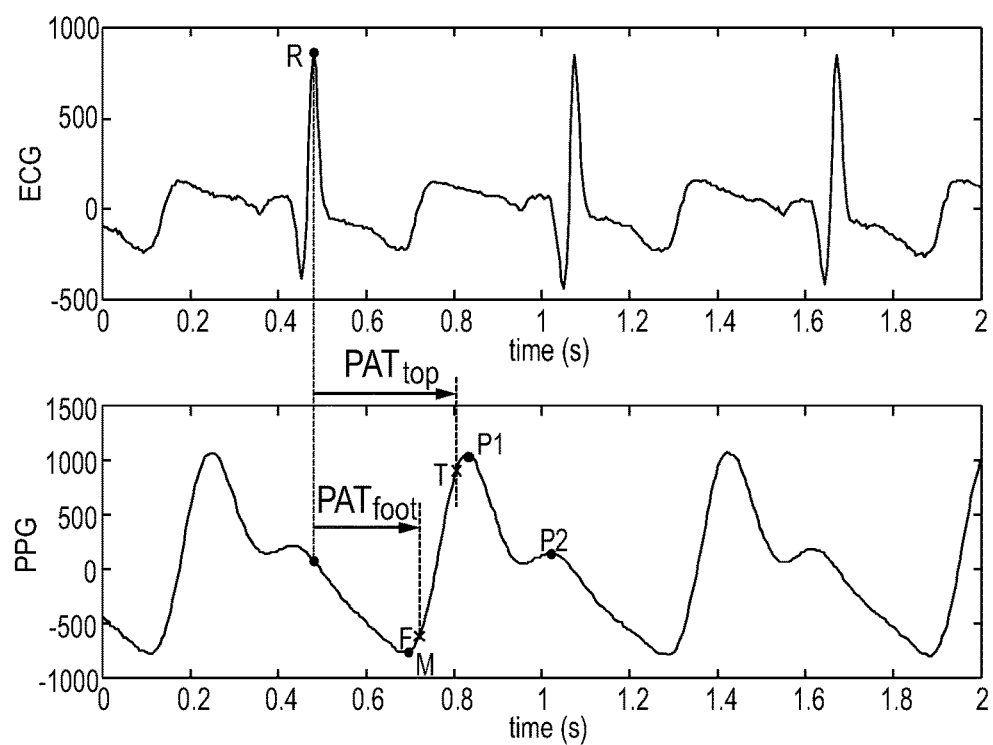
FIG. 2 shows an electrocardiogram and a photoplethysmogram for measuring a pulse arrival time according to the state of the art.

FIG. 2 shows, for illustration purposes, an electrocardiogram and a photoplethysmogram for evaluating the pulse arrival time according to the state of the art. The electrocardiogram and the photoplethysmogram are detected at different positions on the human body in order to measure the pulse transit time and to detect trends in the blood pressure from the pulse arrival time.

The pulse arrival time is usually determined as a time frame from a maximum peak R of the electrocardiogram to a certain point in time of the photoplethysmogram. The pulse arrival time may be detected as a time frame from the maximum R of the electrocardiogram to a minimum value F of the photoplethysmogram as a foot pulse arrival time $PAT_{foot}$ or to a maximum value T of the photoplethysmogram as a top pulse arrival time $PAT_{top}$ or as a time to the maximum slope of the photoplethysmogram between the maximum and the minimum value of the photoplethysmogram.

Figure 3:
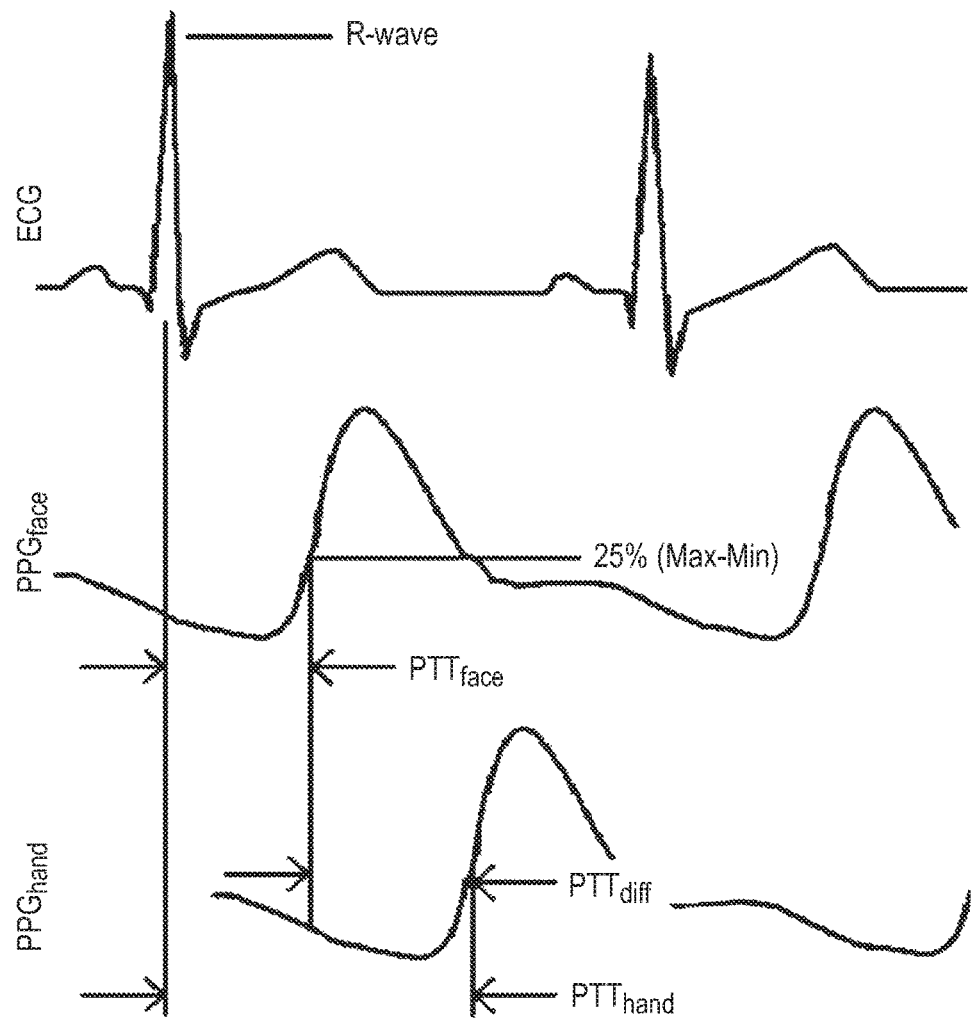
FIG. 3 shows an electrocardiogram and two PPG signals obtained at different locations for illustrating the determination of PTT and PWV.

FIG. 3 shows a diagram of an ECG (as a reference) and two PPG signals, as used according to the present invention, obtained at different body locations, e.g. at the face ($PPG_{face}$) and the hand ($PPG_{hand}$) of a subject. Therein the pulse transit time at the face ($PTT_{face}$) and at the hand ($PTT_{hand}$) are indicated as well as their difference $PTT_{diff}$. The pulse wave velocity PWV is obtained by calculating $PWV=D/PTT_{diff}$, where D is the distance difference between the travelling distances from the heart to the face and the hand, i.e. the positions where the PPG signals were obtained from.

Figure 4A:
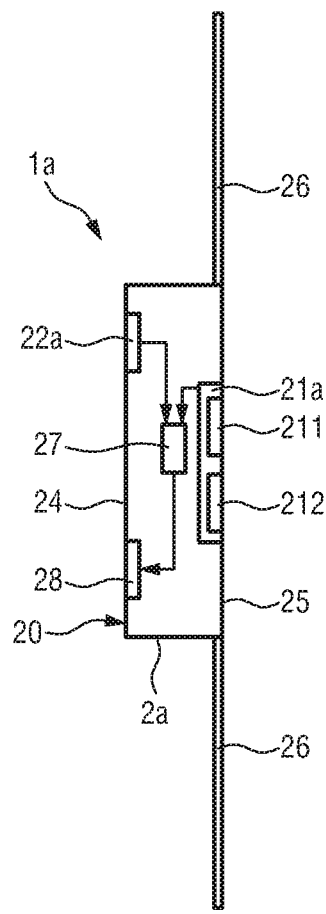
FIG. 4A and FIG. 4B show a second embodiment of a device according to the present invention in the form of a wrist worn device.
Figure 4B:
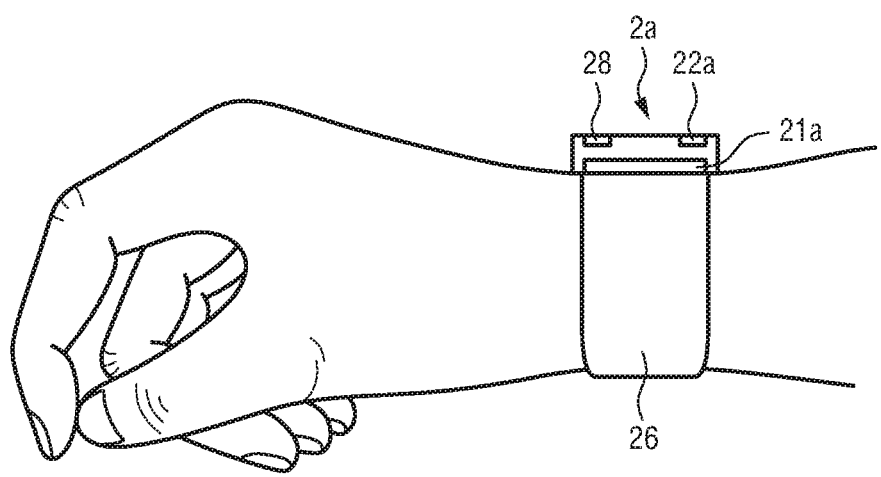

FIG. 4A and FIG. 4B show a second embodiment of a device 2a according to the present invention in the form of a wrist worn device. FIG. 4A shows a cross-sectional side view, FIG. 4B shows the device 2a mounted to the wrist of the subject. In this embodiment the device 2a is wearable on the wrist and may e.g. be a separate device or integrated into a known device, such as a wrist worn watch, smartphone, multimedia player, heart rate monitor, etc. The device 2a comprises, in this exemplary embodiment, two embedded optical sensors arranged on different sides of the device 2a to measure PPG signals of a subject from two different parts of the body.

On a front side 24 of the housing 20 of the device 2a a camera 22a (representing the imaging unit), in particular a 2D camera sensor, is arranged, and on a rear side 25 (facing the skin of the subject, when worn by the subject using the wrist band 26) of the housing 20 a single spot photo-sensor 21a (or, alternatively, 2D camera sensor, representing the PPG signal sensing unit) is arranged. In the current embodiment, the single spot photo-sensor 21a is arranged to contact the skin of the wrist of the subject. A 2D camera sensor can be either monochrome (a single wavelength) sensor, or multi wavelength sensor (e.g. an RGB). The single spot photo-sensor 21 preferably includes, like known pulse oximeters, a dedicated light source 211, preferably in the visible (preferably red) or near infrared spectrum, and a photo detector 212.

In this embodiment the device 2a further integrates a processing unit 27 for deriving a second PPG signal from said sequence of images and for determining the pulse-related information from said first and second PPG signals. As explained earlier, the pulse related information is one of pulse transit time, pulse arrival time, pulse wave velocity, hemodynamic information, blood pressure changes, and combination thereof. This processing unit 27 thus commonly represents the input unit 3 (e.g. a data interface for obtaining the measured data from the sensor 21a and the camera 22a) and the processor 4 for determining the desired pulse-related information of the device 1 shown in FIG. 1. Further, a user interface 28, e.g. a display, is provided for outputting the determined pulse-related information and/or other information derived therefrom (e.g. an indication of the change of blood pressure, a warning, an recommendation, a health status information, etc.). Hence, all elements of the system are commonly integrated into the device 2a.

Figure 5A:
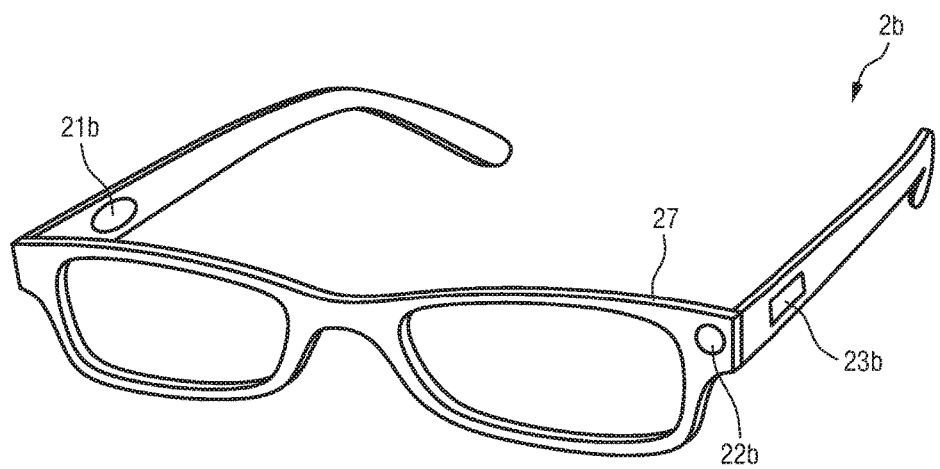
FIG. 5A and FIG. 5B show a third embodiment of a device according to the present invention in the form of glasses.
Figure 5B:
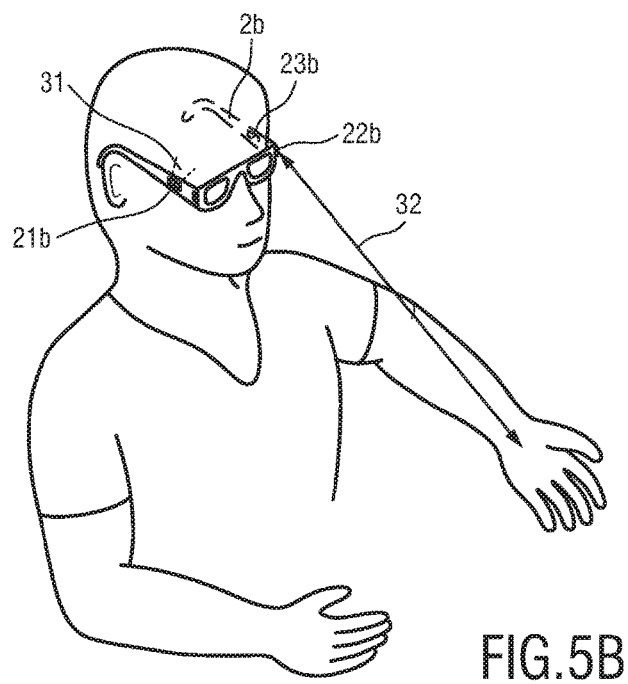

FIG. 5A and FIG. 5B show a third embodiment of a device 2b according to the present invention in the form of glasses. FIG. 5A shows a perspective view of the glasses 2b, FIG. 5B shows the glasses 2b worn by the subject. In this embodiment, a first camera 21b (representing the PPG signal sensing unit) is mounted on the rear side of the frame 27 and a second camera 22b (representing the imaging unit) is mounted on the front side of the frame 27. Both cameras 21b, 22b may be 2D camera sensors for obtaining a sequence of image frames over time, from which respective PPG signals can be derived. As shown in FIG. 5B the first camera 21b faces the face of the user (e.g. the temple, as indicated by 31) and the second camera faces away from the user and can be used to acquire the sequence of images e.g. from the hand or arm (as indicated by 32) of the user of the glasses 2b, who directs his head and/or the arm in a corresponding position. In the current embodiment, when the glasses 2b is worn by the subject, the first camera 21b contacts the skin of the subject in order to acquire the PPG signal.

The other elements of the system may also be integrated into the glasses 2b, similar as explained above with respect to the wrist worn device 2a. Alternatively, as shown in FIG. 5A, the glasses may include an output unit 23b, e.g. a transmitter (e.g. a Wifi or Bluetooth transmitter) for transmitting the respective data to an external entity, e.g. a computer for processing and outputting results.

FIG. 6 shows a fourth embodiment of device 2c according to the present invention in the form of a smartphone. In this embodiment the front side camera 21c is used as a PPG signal sensing unit and rear side camera 22c is used as an imaging unit (or vice versa). The smartphone 2c is used by holding one of the cameras directly in front of or in contact with skin, e.g. of the arm and orienting it such that the other camera faces a different body part, e.g. the face, to obtain different sequences of images from the two cameras 21c, 22c, which can be processed, preferably using the processor of the smartphone, to derive two PPG signals and the desired pulse-related information. Hence, preferably, all elements of the system, i.e. the processing unit 27 and the user interface 28, are commonly integrated into the smartphone 2c.

FIG. 7 schematically shows a fifth embodiment of a device 2d according to the present invention. In addition to the elements of the device 2 shown in FIG. 1, the device 2d further comprises one or more additional elements.

One additional element may be a distance unit 29 for obtaining the distance between said first and second body locations and/or the distance between each of said body locations and the heart to obtain the desired distance difference. In this case the processing unit 27 of the device 2b (or the processor 4 of the external entity 5 in another embodiment) is configured to use the obtained distance difference in determining the pulse-related information. The distance unit 29 may e.g. be configured to obtain the distance(s) through measurement, in particular from an image of the sequence of images acquired by the imaging unit, or through input (e.g. by the user or another person, who measured the distance(s) in advance).

In this way the estimation of blood pressure changes can be further improved by taking into account the distance difference between the different ROIs (regions of interest, i.e. location from which the PPG signal are obtained) and the heart, such as the distance difference between the face and the wrist of a person with respect to the heart. The distance and/or the distance difference can either be estimated automatically, or set manually, or extracted from the known physiological data of a subject.

Another additional element may be an illumination unit 40 mounted in or at the device body 20 for illuminating said first and/or second body locations. This further improves the acquisition of PPG signals and the quality and robustness of the determined pulse-related information.

Still further additional elements may be an image recognition unit 41 for detecting when said second body part is shown in the images of the acquired sequence of images and a control unit 42 for controlling the PPG signal sensing unit 21 to start acquiring the first PPG signal if it is detected that the second body part is shown in an image. In this embodiment, device 2d starts measurement of two PPG signals from different body locations after a person, in particular a desired body location to be used for PPG signal acquisition, such as a face of a person, is detected by the imaging unit 22.

Preferably, according to the present invention optical sensors are used for both the PPG signal sensing unit 21 and the imaging unit 22, e.g. arranged on opposite sides of the device 2 and working at the same wavelength. However, in other embodiments the PPG signal sensing unit 21 is not an optical PPG sensor, but any other sensor to measure a PPG signal, such as a capacitive sensor or a pressure sensor.

In yet another embodiment, the measurements of PPG signals are performed only if no motion of the respective body parts, e.g. the face and/or wrist, is detected for a certain amount of time, which may be detected by an evaluation of the images obtained by the imaging unit 22.

A further improvement may be obtained by use of a calibration measurement with a conventional blood pressure measurement device, which may be used to calibrate the proposed wearable device, in particular blood pressure information obtained with the proposed wearable device. By use of such a calibration it may be possible to derive blood pressure information from the measurements made by the wearable device even without knowing the distance information about the distances between the different body locations or the distance difference discussed above.

This may be refined even further by making use of pattern recognition for recognizing various parts of the body (e.g. the face and/or hand). Individual calibration factors, obtained in advance for the respective body part, may then be applied in the real measurements and calculations by use of the wearable device.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A wearable device for obtaining signals from a subject for use in the monitoring of at least one of pulse transit time and pulse arrival time, said device comprising:
a device body;
a PPG signal sensing unit for acquiring a first photoplethysmography, (PPG), signal from a first body location of the subject's body, wherein the first PPG signal sensing unit is in contact with the first location;
an imaging unit for acquiring a sequence of images from a second body location of the subject's body different from the first body location, said sequence of images being configured for deriving a second PPG signal for the second body location of the subject's body, wherein said PPG signal sensing unit and said imaging unit are mounted in or at the device body and are configured to simultaneously acquire the first PPG signal and the sequence of images;
a distance unit for obtaining at least one of the distance between said first and second body locations and the distances between the first body location and the second body location, respectively, and the heart; and
a processing unit for deriving the second PPG signal from said sequence of images, wherein the processing unit is configured to determine pulse-related information comprising at least one of pulse transit time and pulse arrival time based on the first PPG signal and the second PPG signal, wherein said processing unit is configured to use the obtained distance or distances in determining the pulse-related information.

2. The wearable device as claimed in claim 1, wherein the processing unit determines the at least one of the pulse transit time and the pulse arrival time based on time delay between the peaks of the first PPG signal and the second PPG signal.

3. The wearable device as claimed in claim 1, wherein said PPG signal sensing unit comprises an optical sensing unit, in particular a contact sensor.

4. The wearable device as claimed in claim 1, wherein said PPG signal sensing unit comprises another imaging unit.

5. The wearable device as claimed in claim 1, wherein said distance unit is configured to obtain the distance from an image of the sequence of images acquired by the imaging unit, or through input.

6. The wearable device as claimed in claim 1, further comprising an illumination unit mounted in or at the device body for illuminating at least one of said first and second body location.

7. The wearable device as claimed in claim 1, further comprising an image recognition unit for detecting when said second body location is shown in the images of the acquired sequence of images and a control unit for controlling the PPG signal sensing unit to start acquiring the first PPG signal if it is detected that the second body location is shown in an image.

8. The wearable device as claimed in claim 1, further comprising mounting equipment for mounting the device body at the subject's body.

9. The wearable device as claimed in claim 1, wherein said wearable device is a wrist worn device.

10. The wearable device as claimed in claim 1, wherein said wearable device is a wrist worn device, wherein said PPG signal sensing unit is arranged at the bottom of the device body and the imaging unit is arranged at the front or a side surface of the device body.

11. The wearable device as claimed in claim 1, wherein said PPG signal sensing unit is mounted at a first position in or at the device body facing said first body location when the wearable device is worn by the subject and wherein said imaging unit is mounted at a second position in or at the device body facing said second body location when the wearable device is worn by the subject.

12. The wearable device as claimed in claim 1, wherein said processing unit is further configured to determine at least one of pulse wave velocity, hemodynamic information and blood pressure changes of the subject.

13. The device as claims in claim 1, wherein the wrist worn device is at least one of: a watch, a heart rate monitor, glasses, a camera, a multimedia player, a mobile phone, and a smart phone.

* * * * *